United States Patent [19]

Bernier et al.

[11] Patent Number: 5,371,011
[45] Date of Patent: Dec. 6, 1994

[54] MOLD CONTROL IN FORAGE

[75] Inventors: Roger L. Bernier, Burlington; Anne-Marie M. LaPointe, Vancouver, both of Canada

[73] Assignee: Zeneca Corp., North York, Canada

[21] Appl. No.: 860,529

[22] Filed: Mar. 30, 1992

Related U.S. Application Data

[63] Continuation-in-part of Ser. No. 549,863, Jul. 9, 1990, abandoned.

[30] Foreign Application Priority Data

Jul. 10, 1989 [CA] Canada .................................. 605196

[51] Int. Cl.$^5$ ...................... A01N 63/00; A23K 3/00; C12N 1/00; C12N 1/20
[52] U.S. Cl. ............................ 435/252.4; 424/93.45; 424/93.462; 426/31; 426/53; 426/54; 426/636; 435/252.5; 435/252.9; 435/800; 435/839; 435/857; 435/880
[58] Field of Search ............... 435/252.4, 252.5, 252.9, 435/253.4, 800, 839, 853, 857, 880; 424/93 D, 93 H, 93 J, 93, 93 P, 93 M; 426/18, 31, 49, 52, 53, 54, 635, 636

[56] References Cited

U.S. PATENT DOCUMENTS

| | | | |
|---|---|---|---|
| 4,089,979 | 5/1978 | Jackson | 426/69 |
| 4,266,028 | 5/1981 | Nakamura et al. | 435/118 |
| 4,528,199 | 7/1985 | Moon et al. | 435/857 |
| 4,743,454 | 5/1988 | Tomes | 426/61 |
| 4,762,724 | 8/1988 | Staker et al. | 426/302 |
| 4,789,551 | 12/1988 | Sayle | 426/54 |
| 4,820,531 | 4/1989 | Tomes | 426/52 |
| 4,842,871 | 6/1989 | Hill | 435/851 |
| 4,851,240 | 7/1989 | Day et al. | 426/53 |

FOREIGN PATENT DOCUMENTS 475684 3/1992 European Pat. Off. .
8401317 5/1984 Japan .
751382 7/1980 U.S.S.R. .

OTHER PUBLICATIONS

Burghardi et al., J. Animal Science 50, 729 (1980).
*American Type Culture Collection:* Catalogue of Strains I., 15th ed., 1982, pp. 190–191.

Primary Examiner—Robert J. Warden
Assistant Examiner—L. M. Crawford
Attorney, Agent, or Firm—Gerald A. Gowan

[57] ABSTRACT

Anti-fungal and anti-microbial bacterial strains of *Serratia* are used in the preparation and preservation of animal feedstuffs made from forage. Bacterial strains of *Serratia rubidaea* are particularly useful for such purposes, and permit hay to be baled at higher moisture content. Mixtures of this strain with another anti-fungal bacterial, such as *Bacillus subtilis*, and/or lactic acid-producing bacterial strains, such as strains of *Lactobacillus, Streptococcus, Enterococcus, Lactococcus* and *Pediococcus* are used in the preparation and preservation of silage.

29 Claims, No Drawings

MOLD CONTROL IN FORAGE

CROSS REFERENCE TO RELATED APPLICATION

This application is a continuation-in-part of application Ser. No. 07/549,863, filed Jul. 9, 1990, now abandoned.

FIELD OF THE INVENTION

The present invention relates to anti-fungal bacterial strains, in particular anti-fungal bacterial strains of Serratia, for use in preserving animal feedstuff compositions, including silages and hay.

BACKGROUND OF THE INVENTION

Animal feedstuffs include forages such as cereal grains, whole cereal crops, grasses, legumes, rice, alfalfa, lucerne, sorghum and hay. The forage is usually stored as a dried material, or in the form of a silage produced from these materials by fermentation processes. This fermentation to produce silage is generally conducted in an oxygen-free environment and in the presence of acid-producing bacteria. The dried material or the silage is taken for use as feedstuff as needed.

When a forage is to be stored as a dried material, it is necessary that the material be dried to varying degrees prior to storing in order to minimize the colonization of harmful microbes naturally present. For example, hay in the field carries a complex population of fungi, yeasts, actinomycetes and bacteria which could colonize during storage and lead to, in extreme cases, spontaneous combustion. Also, the development of mould or fungus can lead to palatability and health problems for both animals and humans. The rate of microbial development varies depending upon the moisture content, and for baled hay a moisture content of about 15% is a generally preferred upper limit where microbial activity is reduced to a tolerable level. In North America, in order to achieve this low level of moisture content, the usual practise is to allow a period of field wilting or drying prior to baling.

Silage is the fermentation product of crops, such as those listed hereinbefore, brought about by native lactic acid-producing bacteria present on the crop at harvesting. Lactic acid fermentation can be improved by the addition of selected lactic acid-producing bacteria. Such bacteria include selected lactic acid-producing strains of the genus Lactobacillus, the genus Streptococcus, the genus Enterococcus, the genus Lactococcus and the genus Pediococcus.

It is important that a state of anaerobiosis be attained in order to obtain good silage, and therefore, the crop is usually stored and permitted to ferment in a sealed container or silo. The state of anaerobiosis, however, can be difficult to achieve rapidly, and is governed by the degree to which air comes into contact with the preserving material in the silo. The exposure of silage to air, in particular oxygen in the air, results in spoiling of the silage, and the degree of spoiling will depend on the aerobic stability of the silage. Also, silage material can spoil after having been removed from the silo prior to animal feeding depending upon this elapsed time interval. In these instances, the spoiling is primarily due to yeast or mould contamination of the ensiled material.

Fungal growth in forage can be modified or prevented by the addition of chemical fungicides, such as ammonia or organic acids or their salts, prior to storing, or by various physical means including longer wilting periods in the field, the use of driers, reduction of the oxygen concentration, and/or alteration of pH.

A bacterial strain of the species *Bacillus subtilis* has been disclosed in SU 751382, dated Jul. 30, 1980, to display fungicidal activity in fodder specifically against *Stachybotris alternans* and *Dendrodochium toxicum*.

U.S. Pat. No. 4266028, dated May 5, 1981, discloses the preparation of the anti-fungal antibiotic prodigiosin by cultivation of the bacterium *Serratia marcescens* R-2.

It would be required that any specific biological control agent for use in silage or dried forage would have to operate under a complex set of changing conditions and compete with the natural microflora that are present.

Surprisingly, we have now found bacterial strains that can be used for effectively controlling the growth of fungi, actinomycetes and bacteria in forage. These bacterial strains are mixed with lactic acid-producing bacterial strains for use in producing and preserving silage. In particular, we have found bacterial strains of the genus Serratia that exhibit both anti-fungal and anti-bacterial properties enabling the biological control of several moulds and bacteria in forage.

Therefore, it is an object of the present invention to better prepare and preserve silage by treatment of a suitable material to be ensiled with a mixture of an anti-fungal bacterial strain and a lactic acid-producing bacterial strain.

It is a further object of the present invention to provide anti-fungal bacterial strains that may be used in permitting hay or other dry forage to be baled or stored (preserved) at significantly higher moisture content than normal.

It is yet a further object of the present invention to provide bacterial strains that may be formulated into compositions for use in treating forage.

SUMMARY OF THE INVENTION

Accordingly, in one aspect of the present invention there is provided an animal feedstuff composition comprising a forage and an anti-fungal effective amount of an anti-fungal bacterial strain of the genus Serratia.

Preferably, the anti-fungal bacterial strain is of the species selected from the group consisting of *Serratia rubidaea*, *Serratia plymuthica* and *Serratia liquefaciens*. More preferably, the anti-fungal strain is of the species *Serratia rubidaea*, such as Serratia rubidaea FB299 deposited with the National Collections of Industrial and Marine Bacteria (NCIMB), 23 St. Machar Drive, Aberdeen, Scotland, under accession number NCIMB 40285, on May 23, 1990.

Preferably, the forage of the animal feedstuff composition is hay.

The feedstuff may additionally comprise an anti-fungal effective amount of the anti-fungal bacterial strain Bacillus subtilis FB 260 deposited wit NCIMB under accession number NCIMB 40286, May 23, 1990.

In a preferred embodiment of the invention the animal feedstuff composition further comprises a lactic acid-producing bacterial strain of a genus selected from the group consisting of Lactobacillus, Streptococcus, Enterococcus, Lactococcus and Pediococcus. In the instance where it is desirable that the animal feedstuff composition is a silage, the lactic acid-producing bacterial strain is present in a lactic acid-producing effective amount to effect fermentation to produce silage. Preferably, the lactic acid-producing strain is of the genus Lactobacillus. More preferably, the lactic acid-producing strain is of the species *Lactobacillus plantarum*. Yet more preferably, the lactic acid-producing strain is *Lactobacillus plantarum* MTD 1, a culture of which is deposited at the National collections of Industrial And Marine Bacteria (NCIMB), Aberdeen, Scotland, accession number NCIMB 40027.

In a further aspect of the present invention there is provided a silage composition comprising silage and an anti-fungal effective amount of an anti-fungal bacterial strain of the genus Serratia. Preferably, the anti-fungal bacterial strain is of the species selected from the group consisting of *Serratia rubidaea, Serratia plymuthica* and Serratia liquefaciens. More preferably, the anti-fungal bacterial strain is of the species *Serratia rubidaea*, such as *Serratia rubidaea* FB299.

It will be understood that the silage composition may further comprise the anti-fungal bacteria strain *Bacillus subtilis* FB 260 and/or bacteria of lactic acid-producing strains, as hereinbefore defined, in the instance where such bacteria are used in the preparation of the silage composition.

In yet a further aspect of the present invention there is provided a bacterial composition of use in the preparation and preservation of silage, said composition comprising bacteria of an anti-fungal strain of the genus Serratia in combination with the anti-fungal bacteria strain *Bacillus subtilis* FB260 and/or bacteria of a lactic acid-producing strain of a genus selected from the group consisting of Lactobacillus, Streptococcus, Enterococcus, Lactococcus and Pediococcus. Preferably, the anti-fungal bacterial strain is of the species selected from the group consisting of *Serratia rubidaea, Serratia plymuthica* and *Serratia liquefaciens;* and the lactic acid-producing strain is of the species *Lactobacillus plantarum*. More preferably, the anti-fungal bacterial strain is Serratia rubidaea FB299. Yet, more preferably, the lactic acid-producing strain is *Lactobacillus plantatum* MTD 1, a culture of which is deposited at the National Collections of Industrial And Marine Bacteria (NCIMB), Aberdeen, Scotland, accession number NCIMB 40027.

Preferred characteristics of the anti-fungal bacterial strain of use in the animal feedstuff composition, the silage composition and the bacterial composition of the invention, in addition to having anti-fungal activity (the term "anti-fungal activity" includes activity against moulds or yeast), include: the ability to grow at pH values from about 4.0 to about 8.0; the ability to grow at temperatures from about 15° C. to about 50° C. preferably from about 25° C to about 50° C; the ability to use the carbohydrates glucose, sucrose, melibiose, raffinose, cellobiose, and xylose as a carbon source; weak production of protease; production of cellulases and/or hemicellulases (including xylanases); aerobic and spore-forming, gram positive bacterial cells; facultative non spore-forming, gram negative bacterial cells; and osmotolerance shown by the ability to grow at sodium chloride concentrations from about 1% to about 15%.

Any lactic acid-producing strain of the genus Lactobacillus, the genus Streptococcus, the genus Enterococcus, the genus Lactococcus or the genus Pediococcus that is suitable for making silage may be used in the animal feedstuff composition and the silage composition as defined hereinbefore. Bacterial strains suitable include lactic acid-producing strains of the species *Lactobacillus plantarum, Lactobacillus amylophilus, Lactobacillus casei, Lactobacillus acidophilus, Lactobacillus curvatus, Lactobacillus brevis, Lactococcus lactis, Streptococcus thermophilus, Enterococcus faecium,* and *Enterococcus faecalis.*

In addition to the bacterial strains used in the animal feedstuff and the silage and the bacterial compositions, as defined hereinbefore, bacteria of other lactic acid-producing strains and suitable for use in silage may also be present that are strains of the genus Lactobacillus or the genus Streptococcus different from said strains of the compositions as defined hereinbefore.

In yet a further aspect of the present invention, there is provided the novel bacterial FB299 of *Serratia rubidaea,* a culture of which is deposited under the terms of the Budapest Treaty at the National Collections of Industrial And Marine Bacteria (NCIMB), Aberdeen, Scotland, accession number NCIMB 40285 (May 23, 1990).

In yet a further aspect of the present invention there is provided an anti-fungal composition of use in the preservation of forage, preferably hay or silage, or of use in the preparation of the feedstuff or silage compositions as hereinbefore defined, said anti-fungal composition comprising an effective amount of the bacteria strain *Serratia rubidaea* FB 299; and an acceptable carrier therefor.

The anti-fungal composition may addionally comprise the anti-fungal bacterial strain *Bacillus subtilis* FB 260 and/or a lactic acid-producing strain as hereinbefore defined.

In yet a further aspect of the present invention there is provided a method for the preparation or preservation of an animal feedstuff composition, as described hereinbefore, comprising treating a forage with an effective amount of bacterial cells of an anti-fungal bacterial strain of the genus Serratia. Preferably, the anti-fungal bacterial strain is of the species selected from the group consisting of *Serratia rubidaea, Serratia plymuthica* and *Serratia liquefaciens.* More preferably, the anti-fungal strain is *Serratia rubidaea* FB 299, as hereinbefore defined. Optionally, the method further comprises treating said forage with an effective amount of the anti-fungal strain *Bacillus subtilis* FB 260 and/or bacteria of a lactic acid-producing strain of a genus selected from the group consisting of Lactobacillus, Streptococcus, Enterococcus, Lactococcus and Pediococcus. Preferably, the lactic acid-producing strain is of the species *Lactobacillus plantarum,* and more preferably Lactobacillus plantarum MTD 1, as hereinbefore defined. Also, optionally, the method comprises treating a forage with an effective amount of the bacterial composition as hereinbefore defined. Preferably the forage is hay.

In still yet a further aspect of the present invention there is provided a method for the preparation and preservation of a silage composition, as hereinbefore defined, comprising treating a suitable forage with an effective amount of bacterial cells of an anti-fungal bacterial strain of the genus Serratia; and an effective amount of bacterial cells of a lactic acid-producing bacterial strain of a genus selected from the group consisting of Lactobacillus, Streptococcus, Enterococcus, Lactococcus and Pediococcus; and optionally, the anti-fungal strain *Bacillus subtilis* FB260. Preferably, the anti-fungal bacterial strain is of the species Serratia is selected from the group consisting of *Serratia rubidaea, Serratia plymuthica* and *Serratia liquefaciens;* and the lactic acid-producing strain is of the species *Lactobacillus plantatum.* More preferably, the anti-fungal bacterial strain is *Serratia rubidaea* FB299. Yet, more preferably, the lactic acid-producing strain is *Lactobacillus plantatum* MTD 1, as hereinbefore defined. Optionally, the method comprises treating the forage with an effective amount of the bacterial composition as hereinbefore defined.

DETAILED DESCRIPTION OF THE INVENTION

In the compositions of the present invention, where appropriate, bacterial cells of the anti-fungal strain and the lactic acid-producing strain are suitably present in relative proportions within the range between 1:9 and 9:1. Preferably they are present in substantially equal proportions.

The anti-fungal bacterial strains according to the present invention may be prepared in any required quantity by fermenting a sample of said strain under suitable conditions in an appropriate medium. Such conditions and media are well known in the art. The media will, for example, generally contain a nitrogen source (e.g. fish meal or tryptone) and a carbohydrate source such as starch or glucose. Suitable conditions include a temperature in the range from about 20° C. to about 40° C., and an approximately neutral pH. Fermentation may be conveniently carried out in batches, typically for periods of 1-2 days, or using continuous culture. The living biomass of the bacterial strain may be obtained from the fermentation liquor by concentration, for example by centrifugation or micro or ultra-filtration, followed by addition of any desired and appropriate formulating agents. Formulating agents which may be useful include, for example, surface active agents, e.g., wetting agents, solid diluents, dispersing agents and UV stabilisers. If desired, solid formulations may be prepared by known methods.

In the practise of the method of the present invention, the bacterial composition can be applied as a liquid or a particulate solid. When it is to be applied as a liquid the carrier will be water whilst when it is to be applied as a solid the carrier will be a solid material. Generally compositions to be applied as solids will be supplied to users as complete formulations including the carriers. However, when the composition is to be applied as a liquid, the user will generally be supplied with the appropriate bacterial cells to be suspended in an appropriate volume of water before use.

When the bacterial composition of the invention is to be applied as a solid, any suitable material may be used as a carrier in said composition. Examples of suitable carriers include cereals such as ground corn cobs, ground barley and wheat and other materials such as clay, chalk, magnesite, limestone and talc.

In addition to carriers and bacteria the compositions for use in the preparation of silage will generally contain further materials added for a variety of reasons. Any further material added may be included as another component of the bacterial composition of the invention. Further materials include nutrients (which can be sugars such as sucrose, lactose, etc); growth factors which are necessary for the growth of some bacteria (including yeast extract, corn steep liquor, vitamins and amino acids); materials added to protect the viability of the bacteria; anti-oxidants; materials to assist with oxygen uptake; and oils and other materials to reduce dusting tendencies of the additives or improve adhesion to crops.

The relative proportions of carrier and bacteria included in a composition for use in the preparation of silage depend upon the particular bacterial strain used and upon its activity and viability. A particularly suitable bacterial composition to be applied as a solid will include a solid carrier such as ground corn cobs (maize grits). When the bacterial cells are to form part of a liquid additive for application, they will be suspended by the user in a sufficient amount of water. The concentration of living cells, as defined by the number of Colony Forming Units (CFU), may be used as a guide for determining application rates. As a guide bacterial cells may be applied as a liquid suspension or solid additive in concentrations in the range from about $1 \times 10^5$ CFU to about $1 \times 10^8$ CFU per gram of forage treated depending upon the nature and condition of the forage. Preferably, the concentration is in the range from about $1 \times 10^5$ to about $5 \times 10^6$ CFU per gram of forage.

In the preparation of the animal feedstuff, silage and bacterial compositions of the invention, the bacteria are usually dried by suitable means, e.g. freeze dried or spray dried, or a living culture is resuspended in water, and are then mixed with other components by conventional blending/mixing procedures.

The preparation of the animal feedstuff and silage compositions according to the present invention is generally carried out by applying, such as by spraying, the bacterial cells of the appropriate bacterial strain or bacterial composition as hereinbefore defined to high-moisture corn silage naturally infested or liable to infestation by various microbes.

The living biomass (bacterial cells) undergo their life cycle providing the anti-fungal and anti-bacterial activities required to control spoilage.

The novel bacterial strains and the bacterial composition according to the present invention may be used in the preparation and preservation of a wide variety of forage, including silage and hay that are prone to infestation by moulds. Activity against coliforms and yeast is also observed in some instances, particularly when Bacillus subtilis FB 260 is included as part of the composition. Other advantages include the preservation of colour and the control of heating in the preparation and/or preservation of the animal feedstuff or silage compositions of the invention. This is particularly important in the case of preserved hay, which is graded by colour. Specific examples of commercially important forage to be protected by the invention are legumes, including alfalfa, lucerne, maize, high-moisture corn grains, corn silage, grain silage, grass silage, vegetable silages, and grass and legume hays.

We have found that Serratia rubidaea FB 299 produces lactic acid, and in such cases, when necessary, the presence of an additional lactic acid producing bacteria can be minimized.

A further advantage of the present invention is to provide bacterial strains, and feedstuff, silage and bacterial compositions that are acceptable under appropriate feedstuffs legislation with no undesirable effects on livestock and no by-products therefrom, and produce no residues in said by-products.

A yet further advantage is to provide bacterial strains and said compositions of the present invention that are safer for operators to use and cause no corrosion or damage to machinery.

The following Examples additionally illustrate the invention, but the scope of the invention is not limited to the embodiments shown therein.

EXAMPLE 1

The following example illustrates the isolation of Serratia rubidaea strain FB299 and Bacillus subtilis strain FB260.

A sample of hay was obtained from St. Valerien, Quebec, Canada, and a sample of silage was obtained from "Ferme Brioniman" also in Quebec. Isolation of FB299 and FB260 was carried out by transferring 0.1 g of the hay or silage (1 g of corn) sample, respectively, into 10 ml 0.05% peptone and performing serial dilutions to $10^4$ to $10^7$ depending on how turbid the sample appeared. 0.1 ml of the dilution higher than the one desired was plated using the spread plate method, onto Nutrient-, Yeast-malt, Sabouraud-dextrose and L-S Differential Media. The plates were examined after 5 days incubation at room temperature. The colonies were selected and purified on the medium of isolation and were incubated until growth at room temperature. Slides were made of the chosen colonies, were gram stained and observed under the microsocope (at a magnification of 1000X using the oil immersion lens) for further characterization. Bacterial isolates were transferred to nutrient agar slants and stored at 4° C. prior to use.

Table 1 lists the morphological and microbiological characteristics of the strains Bacillus subtilis FB260 and Serratia rubidaea FB299.

TABLE 1
MORPHOLOGY AND MICROBIOLOGICAL CHACTERIZATION

FB260: Aerobic and spore-forming bacterium, gram positive individual cells, colonial morphology typical of Bacillus species
growth observed at pHs varying from 4.5 to 8.0
growth observed at temperatures varying from 25 to 50° C.
growth observed at final NaCl concentration varying from 1 to 15%
the strain can use, as a carbon source, glucose, sucrose, melibiose, raffinose, cellobiose and xylose
the strain is a weak producer of proteases, but a strong producer of amylases and xylanases
the strain has shown anti-fungal effect against many moulds particularly against Penicillium sp, Absidia sp, Aspergillus niger and Aspergillus flavus.

FB299: Facultative and non spore-forming bacterium, gram negative individual cells,
growth observed at pHs varying from 4.0 to 8.0
growth observed at temperatures varying from 25 to 50° C.
growth observed at final NaCl concentration varying from 1 to 10%
the strain can use, as a carbon source, glucose, sucrose, melibiose, raffinose, cellobiose and xylose
the strain has shown anti-fungal effect against many moulds particularly against Penicillium sp, Absidia sp, Aspergillus niger and Aspergillus flavus.

EXAMPLE 2

This example illustrates the application of bacterial strains FB260 and FB299, and a mixture of these strains, for preserving alfalfa hay.

500 g of alfalfa hay were weighed out in a plastic bucket on a scale. Each sample was placed in a separate pile on a plastic sheet. There were 8 replications per treatment so 8 piles were arranged at a time. Each pile was sprayed with 10 ml of the appropriate treatment strain using SpotGUN-Lurmark spray guns. Hay was rearranged in each pile and proceeded to spray a further 10 ml onto each sample. This was done so that a better coverage of the alfalfa was obtained. The samples were then bagged individually in nylon mesh bags by packing the alfalfa tightly as a "bale", wiring the bags shut and labelling them. This procedure was followed for each treatment, 1 through 3 resulting in 24 "bales" of hay at each moisture level 40% and 28%. The bales were piled in two piles, according to the moisture content, on the floor in an environmental chamber set at 26° C. and 70% relative humidity. After two weeks time a single bale from each moisture level was opened and checked for moisture content using a microwave oven and scale. The experiment was stopped and mould spoilage assessment was conducted. For statistical testing the +/− rating system used in assessing the visual moulds were converted to discrete values based on the following system. A minus (−) was assigned a value of 0%. A plus (+) was assigned a value of 33%. A double plus (++) was assigned a value of 66% and finally a triple plus (+++) was assigned a value of 99%. These percentages were based on the maximum amount of moulds growth a sample could incur before being classified into the next highest rating. The results are listed in Table 2 and show that on the 28% and 40% moisture hay, FB299, FB260 and the mixture provided for good control of moulds.

TABLE 2

| | I. 28% Moisture Level: | | | | | | | |
|---|---|---|---|---|---|---|---|---|
| | Presence of Moulds* on Each "Bale" | | | | | | | |
| Treatment | 1 | 2 | 3 | 4 | 5 | 6 | 7 | 8 |
| 1. Control | + | +++ | ++ | +++ | ++ | ++ | +++ | +++ |
| 2. FB260 | + | + | + | ++ | ++ | + | + | + |
| 3. FB299 | +++ | ++ | ++ | + | + | − | ++ | + |
| 4. FB260 & FB299 | + | +++ | + | +++ | +++ | ++ | ++ | +++ |

| | TREATMENT | | | |
|---|---|---|---|---|
| | Control | FB299 | FB260 | Mixture |
| Mean Percentage of Visual Moulds | 78 | 49 | 41 | 74 |

| | II. 40% Moisture Level: | | | | | | | |
|---|---|---|---|---|---|---|---|---|
| | Presence of Moulds* on Each "Bale" | | | | | | | |
| Treatment | 1 | 2 | 3 | 4 | 5 | 6 | 7 | 8 |
| 1. Control | +++ | +++ | +++ | +++ | +++ | +++ | +++ | +++ |
| 2. FB260 | +++ | + | +++ | + | +++ | +++ | ++ | +++ |
| 3. FB299 | − | ++ | + | + | − | ++ | +++ | +++ |

TABLE 2-continued

| 4. FB260 & FB299 | +++ | ++ | + | ++ | ++ | ++ | +++ | +++ |
|---|---|---|---|---|---|---|---|---|

| TREATMENT | Control | FB299 | FB260 | Mixture |
|---|---|---|---|---|
| Mean Percentage of Visual Moulds | 99 | 78 | 49 | 74 |

* Visual Moulds Legend:
− No Moulds Growth
+ Slight Moulds Growth
++ Fair Amount of Moulds Growth
+++ Large Amount of Moulds Growth

EXAMPLE 3

The following example shows a comparison of the application of FB299 alone or in combination with *Lactobacillus plantatrum* (Ecosyl, trade mark) to ensiled high-moisture corn grains.

2 kg of high-moisture corn grain for each sample was weighed out and placed in oxygen-impermeable polyethylene bags. 100 ml of the appropriate treatment was poured into the sample bag which was then sealed shut and inverted rapidly 10 times to ensure complete coverage. The final total concentration of living cells applied ranged from $1 \times 10^5$ to $1 \times 10^7$ CFU/g of corn (with an excess of the FB 260 and FB299 when used in combination with the "Ecosyl"). The test included 3 replicates for each of 4 sampling times to give 12 bags per treatment. Nine of the 12 samples belonging to each treatment were placed in separate 75-L galvanized steel garbage bins and covered with a 20 kg sandbag to mimic a silo's pressure. Finally the lids were shut on the 10 "silos". The remaining 3 samples per treatment represented time 0 and were placed in a fridge to halt any activity before the samples could be visually analyzed and their supernatants collected the next day. After 7 days at room temperature, the remaining replicates of each treatment were placed in an environmental chamber at 25.2° C. and 70% relative humidity for the remaining 8 days. At each sampling time, the appropriate samples were visually assessed for mould spoilage and washed with water to collect volatile acids, water-soluble carbohydrates, etc for analytical purposes.

Treatments were conducted according to the following:

Treatment 1 : Control
Treatment 2 : FB299
Treatment 3 : *Lactobacillus plantatum*
Treatment 4 : *Lactobacillus plantarum* +FB299

The results are listed in Table 3 and show that under the conditions described above, all treatments showed less moulds contamination than the control when silage was tested after 15 days. For aerobic stability, treatments #2 and #4 showed both good control of moulds and less temperature increase after 5 days of air exposure. In respect of pH, particulary good values (<4.2) were observed with treatment #4 as compared with the control. FB299 was found to work well in combination with Lactobacillus plantatum to lead to a better silage than the Lactobacillus plantarum strain alone.

TABLE 3

| TREATMENT | VISUAL MOULDS* | pH* | AEROBIC STABILITY** |
|---|---|---|---|
| 1 | 77% | 4.35 | 77%(29.7° C.) |
| 2 | 55% | 4.32 | 33%(23.7° C.) |
| 3 | 55% | 4.21 | 55%(26.7° C.) |
| 4 | 44% | 4.14 | 44%(25.0° C.) |

*Tests conducted after 15 day-old silage
**Tests conducted after the ensilage material was exposed to air for 5 days, at room temperature. The values in percentages are mould spoilage whereas the values between brackets are averaged temperatures.

The embodiments of the present invention in which an exclusive property or privilege is claimed are defined as follows.

1. An animal feedstuff composition comprising a forage and an anti-fungal effective amount of an anti-fungal bacterial strain wherein said strain is *Serratia rubidaea* FB299, a culture of which is deposited at the National Collections of Industrial and Marine Bacteria (NCIMB), Aberdeen, Scotland, under accession number NCIMB 40285.

2. An animal feedstuff as claimed in claim 1 additionally comprising an anti-fungal effective amount of the anti-fungal bacterial strain Bacillus subtilis FB260, a culture of which is deposited at the National Collections of Industrial And Marine Bacteria (NCIMB), Aberdeen, Scotland, under accession number NCIMB 40286.

3. An animal feedstuff composition as claimed in claim 1, wherein said forage is hay.

4. An animal feedstuff composition as claimed in claim 3 further comprising a lactic acid-producing bacterial strain of a genus selected from the group consisting of Lactobacillus, Streptococcus, Enterococcus, Lactococcus and Pediococcus.

5. An animal feedstuff composition as claimed in claim 1, further comprising a lactic acid-producing bacterial strain of a genus selected from the group consisting of Lactobacillus, Streptococcus, Enterococcus, Lactococcus and Pediococcus in a lactic acid-producing effective amount to effect fermentation to produce silage.

6. An animal feedstuff composition as claimed in claim 5, wherein said lactic acid-producing strain is of the genus Lactobacillus.

7. An animal feedstuff composition as claimed in claim 6, wherein said lactic acid-producing strain is of the species Lactobacillus plantarum.

8. An animal feedstuff composition as claimed in claim 7, wherein said lactic acid-producing strain is Lactobacillus plantarum MTD 1, a culture of which is deposited at the National Collections of Industrial And Marine Bacteria (NCIMB), Aberdeen, Scotland, accession number NCIMB 40027.

9. A method for the preparation or preservation of an animal feedstuff composition, as claimed in claim 1, comprising depositing onto a forage an anti-fungal effective amount of bacterial cells of an anti-fungal strain wherein said strain is *Serratia rubidaes* FB299, a culture of which is deposited at the National Collections of Industrial and Marine Bacteria (NCIMB), Aberdeen, Scotland, under accession number NCIMB 40285.

10. A method as claimed in claim 9, further comprising an anti-fungal effective amount of the bacterial strain *Bacillus subtilis* FB260, a culture of which is deposited at the National Collections of Industrial And Marine Bacteria (NCIMB), Aberdeen Scotland, accession number NCIMB 40286.

11. A method as claimed in claim 9 further comprising depositing onto said forage an effective amount of bacteria of a lactic acid-producing strain of a genus selected from the group consisting of Lactobacillus, Streptococcus, Enterococcus, Lactococcus and Pediococcus.

12. A method as claimed in claim 11, wherein said forage is hay.

13. A method as claimed in claim 9, wherein said forage is hay.

14. A silage composition comprising silage and an anti-fungal effective amount of an anti-fungal bacterial strain wherein said strain is *Serratia rubidaea* FB299, a culture of which is deposited at the National Collections of Industrial and Marine Bacteria (NCIMB), Aberdeen, Scotland, under accession number NCIMB 40285.

15. A silage composition as claimed in claim 14, further comprising the anti-fungal bacterial strain *Bacillus subtilis* FB260, a culture of which is deposited at the National Collections of Industrial And Marine Bacteria (NCIMB), Aberdeen, Scotland, under accession number NCIMB 40286.

16. A silage composition as claimed in claim 14, further comprising bacteria of a lactic acid-producing strain of a genus selected from the group consisting of Lactobacillus, Streptococcus, Enterococcus, Lactococcus and Pediococcus.

17. A bacterial composition of use in the preparation and preservation of silage, said composition comprising bacteria of the strain *Serratia rubidaea* FB299, a culture of which is deposited at the National Collections of Industrial and Marine Bacteria (NCIMB), Aberdeen, Scotland, under accession number NCIMB 40285; and bacteria of a lactic acid-producing strain of a genus selected from the group consisting of Lactobacillus, Streptococcus, Enterococus, Lactococcus, and Pediococcus.

18. A bacterial composition as claimed in claim 17, further comprising the anti-fungal strain *Bacillus subtilis* FB260, a culture of which is deposited at the National Collections of Industrial and Marine Bacteria (NCIMB), Aberdeen, Scotland, accession number NCIMB 40286.

19. A bacterial composition as claimed in claim 17, wherein said lactic acid-producing strain is of the genus Lactobacillus.

20. A bacterial composition as claimed in claim 19, wherein said lactic acid-producing strain is of the species *Lactobacillus plantarum*.

21. A bacterial composition as claimed in claim 20, wherein said lactic acid-producing strain is *Lactobacillus platarum* MTD 1, a culture of which is deposited at the National Collections of Industrial And Marine Bacteria (NCIMB), Aberdeen, Scotland, accession number NCIMB 40027.

22. A method for the preparation or preservation of an animal feedstuff composition comprising treating a forage with an effective amount of a bacterial composition as claimed in claim 17 or claim 20.

23. A method as claimed in claim 22, wherein said forage is hay.

24. The biologically pure bacterial strain *Serratia rubidaea* FB299, a culture of which is deposited at the National Collections of Industrial And Marine Bacteria (NCIMB), Aberdeen, Scotland, accession number NCIMB 40285.

25. An anti-fungal composition of use in the preservation of forage or of use in the preparation of a feedstuff composition, comprising an anti-fungal effective amount of the bacterial strain Serratia rubidaea FB299, as claimed in claim 24, and an acceptable carrier therefor.

26. A method for the preparation of a silage composition, comprising depositing onto a suitable forage an anti-fungal effective amount of bacterial cells of an anti-fungal bacteria of the strain *Serratia rubidaea* FB299, a culture of which is deposited at the National Collections of Industrial and Marine Bacteria (NCIMB), Aberdeen, Scotland, under accession number NCIMB 40285; and an effective amount of bacterial cells of a lactic acid-producing bacterial strain of a genus selected from the group consisting of Lactobacillus, Streptococcus, Enterococus, Lactococcus, and Pediococcus.

27. A method as claimed in claim 26, additionally comprising an anti-fungal effective amount of the bacterial strain *Bacillus subtilis* FB260, a culture of which is deposited at the National Collections of Industrial And Marine Bacteria (NCIMB), Aberdeen, Scotland, accession number NCIMB 40286.

28. A method as claimed in claim 26, wherein said lactic acid-producing strain is of the species *Lactobacillus plantarum*.

29. A method as claimed in claim 28, wherein said lactic acid-producing strain is *Lactobacillus plantarum* MTD 1, a culture of which is deposited at the National Collections of Industrial and Marine Bacteria (NCIMB), Aberdeen, Scotland, accession number NCIMB 40027.

* * * * *